United States Patent
Lewarchik

(10) Patent No.: US 11,839,622 B1
(45) Date of Patent: Dec. 12, 2023

(54) CONSUMABLE NUTRACEUTICAL COMPOSITION

(71) Applicant: Randall Lewarchik, Grosse Pointe, MI (US)

(72) Inventor: Randall Lewarchik, Grosse Pointe, MI (US)

(*) Notice: Subject to any disclaimer, the term of this patent is extended or adjusted under 35 U.S.C. 154(b) by 33 days.

(21) Appl. No.: 17/150,432

(22) Filed: Jan. 15, 2021

Related U.S. Application Data

(60) Provisional application No. 62/961,285, filed on Jan. 15, 2020.

(51) Int. Cl.

| | | |
|---|---|---|
| A61K 31/706 | (2006.01) | |
| A23L 33/175 | (2016.01) | |
| A61K 31/137 | (2006.01) | |
| A61K 31/205 | (2006.01) | |
| A61K 31/357 | (2006.01) | |
| A61K 31/05 | (2006.01) | |
| A61K 31/09 | (2006.01) | |
| A61K 36/42 | (2006.01) | |
| A23L 33/105 | (2016.01) | |
| A61K 31/353 | (2006.01) | |

(52) U.S. Cl.
CPC .......... *A61K 31/706* (2013.01); *A23L 33/105* (2016.08); *A23L 33/175* (2016.08); *A61K 31/05* (2013.01); *A61K 31/09* (2013.01); *A61K 31/137* (2013.01); *A61K 31/205* (2013.01); *A61K 31/353* (2013.01); *A61K 31/357* (2013.01); *A61K 36/42* (2013.01)

(58) Field of Classification Search
CPC ...... A61K 31/706; A61K 31/05; A61K 31/09; A61K 31/137; A61K 31/205; A61K 31/353; A61K 31/357; A61K 36/42; A23L 33/175; A23L 33/105
USPC .......................................................... 514/52
See application file for complete search history.

(56) References Cited

U.S. PATENT DOCUMENTS

| | | | |
|---|---|---|---|
| 5,262,162 A | 11/1993 | Bormann et al. | |
| 6,261,589 B1 | 7/2001 | Pearson et al. | |
| 7,678,363 B2 | 3/2010 | Barlow et al. | |
| 7,985,756 B2 | 7/2011 | Barlow et al. | |
| 8,168,225 B2 | 5/2012 | Casana Giner et al. | |
| 8,563,038 B2 | 10/2013 | Andersen et al. | |
| 8,986,664 B2 | 3/2015 | DiColandrea et al. | |
| 9,526,793 B1 | 12/2016 | Kramer et al. | |
| 10,111,831 B2 | 10/2018 | Purcell | |
| 10,195,163 B2 | 2/2019 | Brocia | |
| 2004/0077556 A1* | 4/2004 | Chinery | A61K 36/82 514/567 |
| 2005/0202109 A1 | 9/2005 | Palu et al. | |
| 2007/0190187 A1 | 8/2007 | Kneller et al. | |
| 2008/0038367 A1 | 2/2008 | Saloum | |
| 2010/0272798 A1 | 10/2010 | Akiyama et al. | |
| 2012/0003274 A1 | 1/2012 | Brand et al. | |
| 2018/0055849 A1 | 3/2018 | Allison et al. | |
| 2018/0055850 A1 | 3/2018 | Allison et al. | |
| 2018/0236016 A1 | 8/2018 | Gamay | |
| 2021/0220422 A1* | 7/2021 | Parker | A61K 36/28 |

FOREIGN PATENT DOCUMENTS

| | | |
|---|---|---|
| JP | 4319735 | 8/2009 |
| WO | 2011040697 | 4/2011 |

OTHER PUBLICATIONS

Escande et al. Flavonoid Apigenin Is an Inhibitor of the NAD+ase CD38. Diabetes 62:1084-1093, 2013. (Year: 2013).*
"The Therapeutic Potential of Apigenin—MDPI" found at https://www.mdpi.com, Int. J. Mol. Sci. 2019, 20 (6), 1305.
"Herbal Antidepressants: For anxiety" found at https://www.indigo-herbs.co.uk, https://www.indigo-herbs.co.uk/natural-health-guide/benefits/herbal-antidepressants (accessed on Jan. 15, 2021).
"Chronic Effects of a Wild Green Oat Extract Supplementation on Cognitive Performance in Older Adults: A Randomised, Double-Blind, Placebo-Controlled, Crossover Trial" found at https://www.ncbi.nim.nih.gov, Nutrients 2012, 4(5), 331-342.

* cited by examiner

*Primary Examiner* — Yih-Horng Shiao
(74) *Attorney, Agent, or Firm* — David Colls; Berger Singerman LLP

(57) ABSTRACT

The present invention relates generally to a composition comprising apigenin, phenylethylamine, nicotinamide mononucleotide and/or nicotinamide riboside, and resveratrol, anthocyanin, and/or pterostilbene and piceatannol. The composition may be provided in the form of a beverage, jell packet, mixable powder, or the like. Alternatively, the composition may be microencapsulated and selectively added to a consumable substance, such as a fluid, jell, or the like. The composition may be used to increase the consumer's levels of energy, alertness, and activate the body's natural chemical that prevent anxiety and depression. Furthermore, the inclusion of apigenin provides additional benefits, namely, inhibiting the increase of proteins such as CD38 that would otherwise affect the levels of NAD+ in the body that help with cellular aging.

19 Claims, 1 Drawing Sheet

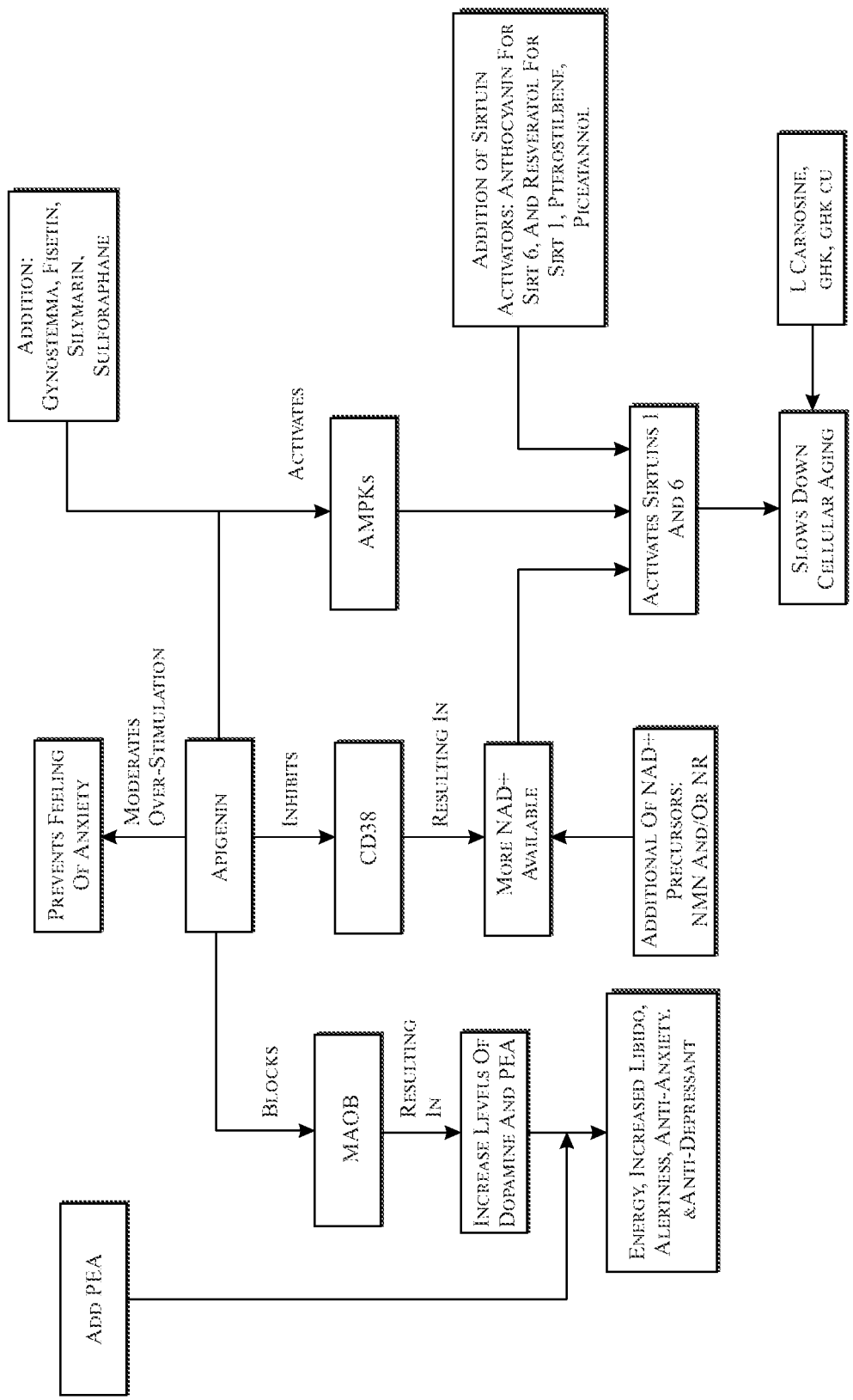

CONSUMABLE NUTRACEUTICAL COMPOSITION

CROSS-REFERENCE TO RELATED APPLICATIONS

This application claims the benefit of United States Provisional Patent Application Ser. No. 62/961,285 filed on Jan. 15, 2020, which is incorporated herein in its entirety.

FIELD OF THE INVENTION

The present invention relates generally to compositions, and more particularly, to a consumable composition generally comprising apigenin, phenylethylamine, nicotinamide mononucleotide, anthocyanin, and/or pterostilbene, piceatannol, resveratrol, and potentially other sirtuin activators. The composition may be used to increase the consumer's levels of energy, alertness, and elevates the body's natural chemicals that prevent anxiety and depression. Furthermore, the inclusion of apigenin provides additional benefits or a second prong of benefits. Namely, inhibiting the increase of proteins such as CD38 that would otherwise affect the levels of NAD+ in the body.

BACKGROUND OF THE INVENTION

Americans are often told that upholding a healthful sleep habit contributes to a plethora of benefits, including but not limited to maintaining proper energy levels, improving the immune system, and reducing stress. Despite the widespread warning by those in the medical field against not receiving enough sleep, or of not obtaining quality sleep, many Americans still do not make time for it. This reluctance to secure enough sleep is partially derived from misinformation about the quantity and quality of sleep that is needed (as many individuals still function with a lesser amount), or the unfortunate fact that some just do not have the appropriate time for a lengthy, restful night of sleep. In fact, a study by the Centers for Disease Control and Prevention reported 1 in 3 Americans do not get enough sleep. Evidence also suggests that this is a global epidemic, as a study across 12 countries and 12,000 participants concluded that 51% of the global population is receiving less sleep than required.

Aside from the individual harm caused by sleep deprivation, such as the potential advancement of morbidity, there is also a societal impact to this epidemic. According to the National Sleep Foundation, being awake for 18 hours straight makes you drive as if you have a blood alcohol level of .05, whereas .08 is generally considered drunk. Despite all this, it is not considered illegal to drive while drowsy and millions still do it daily. Whether brought about by society's tendency to achieve maximal productivity, or simply a habit not considered by most as destructive, sleep deprivation's effects are widespread and hazardous. Other than raising awareness and promoting change of habits, there is one solution that has been developed and popularized—artificial energy boosters. To counteract the lack of energy sustained by individuals whom are either not making the right decision when it comes to healthful sleep habits, or simply do not have the time for adequate sleep due to their circumstances, energy boosts have been famously utilized, typically in a beverage format.

The so-called "energy drinks" originated from the mainstream soft drink industry, which were originally labeled as energy boosters simply because of their higher than average caffeine and sugar content. Efforts were made by a Japanese company in the 1960s to dissociate energy drinks from the soft drink industry, and included more chemicals other than just caffeine and sugar tailored to providing energy, such as essential vitamins, taurine, and niacin. This was coincidentally the point at which sleep deprivation began plaguing the global population, as a study from prominent universities found that nearly two hours of sleep per night has been shaved off our regular sleep cycle since the 1960s. As sleep deprivation became more prevalent, so too did the research and sales of these energy boosters. With better experiments and understanding of the impact of different chemicals on the energy levels of humans, a greater number of unique energy drinks entered the market, claiming that their new recipe was healthier and provided a more prolonged effect.

One constant set of ingredients in most of the energy drinks available for consumption is sugar and caffeine. Although these are proven to increase energy levels, their effect does not persist for long, and the well-known "sugar crash" (an episode of reactive hypoglycemia that occurs a few hours upon consuming a large amount of sugars or carbohydrates) generate even more fatigue than before. On the other hand, consuming excessive amounts of caffeine can induce anxiety, promote jitteriness, and often lead to a greater susceptibility to stress. These are rough side effects to battle when merely an effective boost of energy is sought after. If one's necessity for energy is so drastic that energy boosts are frequently required throughout the week, consuming these beverages can exacerbate existing medical conditions, along with potentially developing new ones, such as: chronic fatigue, diabetes, cardiovascular diseases, and so on.

Another major downfall with available energy boosters is the short duration of its effect. This is not only realized by the ingredients' lack of success for providing long-term energy, but also by their rapid ingestion and breakdown. The contents of the energy drink are exposed to our metabolic processes instantly upon ingestion, and there are currently no methods that extend their effects so that the same dosage can provide energy for hours upon hours.

Not only is there a need for those who need long-term energy because of their hectic lifestyles, there is a need for a consumable for people who suffer from diseases that affect their ability to go about their daily routine. For example, someone suffering from lyme disease may suffer from a vast array of symptoms including narcolepsy and some form of cataplexy, which affects the person's ability to be productive. People who suffer from lyme disease or other diseases that bring an onset of fatigue have a difficult time completing easy tasks that are achievable by those who don't have the disease. Physicians typically prescribe a stimulant such as Adderall® or Nuvigil® to combat symptoms brought on by the disease and an attempt to raise the energy level of the person. However, even powerful stimulants such as those often fall short of their expectations.

As substantiated, there is a unique niche that has yet to be occupied when it comes to the effectiveness of consumable beverages that increase the consumer's levels of energy and alertness. Boosts of energy are desirable for millions of individuals, but it comes at an unnecessary cost of dealing with the side effects of its contents. Accordingly, there is an established need that remains to be solved, but as of yet has been unmet, for a consumable matrix or composition that can provide the consumer with a variety of benefits, including energy for a long period of time, while obviating undesirable side effects associated with known compositions. The desired composition should include a number of desirable effects, including the inhibition of an increase of proteins that would otherwise affect the levels of NAD+ in the body that help with cellular aging.

SUMMARY OF THE INVENTION

The present invention provides a unique composition that effectively increases the levels of energy, alertness, empathy, and libido of an individual, while suppressing the chemicals that are responsible for mood swings, anxiety, and depression.

Introducing a first implementation of the invention, the present invention consists of a nutraceutical composition, comprising: apigenin, phenylethylamine, nicotinamide mononucleotide, anthocyanin, and resveratrol, and in some instances pterostilbene, piceatannol or alternative sirtuin activators, wherein the apigenin eliminates undesirable side effects of the consumption of phenylethylamine, and the composition is selectively mixable with a consumable substance.

In a secondary implementation of the present invention, a nutraceutical composition, comprising: apigenin, phenylethylamine, nicotinamide mononucleotide, resveratrol, anthocyanin extract, gynostemma, fisetin, sulforaphane, and silymarin, wherein the apigenin eliminates undesirable side effects of the consumption of phenylethylamine, wherein gynostemma, fisetin, sulforaphane, and silymarin increase the activation of 5' adenosine monophosphate-activated protein kinase, and wherein the composition is selectively mixable with a consumable substance.

In another aspect, the composition may further comprise L-carnosine.

In a third implementation of the present invention, a nutraceutical composition, comprising, apigenin, phenylethylamine, nicotinamide mononucleotide, resveratrol, anthocyanin extract, liposomal of phytosome GHK-Cu, GHK, collagen peptides, and liposomal vitamin C, wherein the apigenin eliminates undesirable side effects of the consumption of phenylethylamine.

In a fourth implementation of the present invention, a nutraceutical composition, comprising: apigenin, phenylethylamine, nicotinamide mononucleotide, resveratrol, anthocyanin extract, hydroxymethylbutyrate, creatine, and leucine, wherein the apigenin eliminates undesirable side effects of the consumption of phenylethylamine.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which:

FIG. 1 presents a block diagram of how apigenin interacts and enhances the benefits of other ingredients used in the composition Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The terminology used herein is for the purpose of describing particular embodiments only and is not intended to be limiting of the invention. As used herein, the indefinite articles "a", "an" and "the" should be understood to include plural reference unless the context clearly indicates otherwise.

The phrase "and/or," as used herein, should be understood to mean "either or both" of the elements so conjoined, i.e., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including", "includes", "having", "has", "with", or variants thereof, are intended to be inclusive similar to the term "comprising."

As used herein, the term "component" or "components" refer to an elemental or composite molecule of any of a variety of therapeutic chemicals which may be naturally occurring in certain plants and/or animals and/or derived therefrom, or which may be wholly manufactured molecules which have no naturally occurring counterparts, and include, but are in no manner limited to, biologics and pharmaceutical compositions, and which may be incorporated into a formulation of the present invention.

As used herein, the term "formulation" or "matrix" are used interchangeably and refers to any combination of two or more components, as defined hereinabove, intended to elicit a desired physiological response from a person that consumes the formulation.

A formulation in accordance with the present invention may also include or be packaged with other non-toxic compounds, such as pharmaceutically acceptable carriers, excipients, binders and fillers including, but not limited to, glucose, lactose, gum acacia, gelatin, mannitol, xanthan gum, locust bean gum, galactose, oligosaccharides and/or polysaccharides, starch paste, magnesium trisilicate, talc, corn starch, starch fragments, keratin, colloidal silica, potato starch, urea, dextrans, dextrins, and the like. Specifically, the pharmaceutically acceptable carriers, excipients, binders, and fillers contemplated for use in the practice of the present invention are those which render the compounds of the invention amenable for delivery to a patient by any of a variety of delivery mechanisms including, but not limited to, orally, intravenous, transdermal, topical, inhalation, and the like. Moreover, the packaging material may be biologically inert or lack bioactivity, such as plastic polymers, silicone, etc., which may be processed internally by the subject without affecting the efficacy of the formulation packaged and/or delivered therewith.

The term "therapeutically effective amount" as used with reference to the present formulation and/or components thereof as described herein refers to the quantity of the nutraceutical formulation and/or components thereof necessary to render the desired therapeutic result. For example, an effective amount is a level effective to treat, cure, or alleviate the symptoms of a disorder for which the nutraceutical formulation is being administered. Amounts effective for the particular therapeutic goal sought will depend upon a variety of factors including: the disorder being treated and its severity; the bioavailability, and activity of the specific compound, biologic or pharmaceutical composition used; the route or method of administration and introduction site on the subject; the rate of clearance of the specific compound or biologic and other pharmacokinetic properties; the duration of treatment; inoculation regimen; drugs used in combination or coincident with the specific compound, biologic or composition; the age, body weight, sex, diet, physiology and general health of the subject being treated; and like factors well known to one of skill in the relevant scientific art. Some variation in dosage will necessarily occur depending upon the condition of the subject being treated, and the physician or other individual administering treatment will, in any event, determine the appropriate dosage for each individual person.

As used herein, the term "administering" refers to providing a therapeutically effective amount of the present nutraceutical formulation and/or components thereof to a person via any of a number of potential delivery mechanisms including, but not limited to, oral, intravenous, transdermal, topical and/or inhalation, and the like. The formulation and/or components thereof of the present invention can be administered individually, but may also be administered with other compounds, excipients, fillers, binders, carriers or other vehicles selected based upon the chosen route of administration and standard pharmaceutical practice. Administration may be by way of carriers or vehicles, such as injectable solutions, including sterile aqueous or non-aqueous solutions, or saline solutions; creams; lotions; capsules; tablets; granules; pellets; powders; suspensions, emulsions, or microemulsions; patches; micelles; liposomes; vesicles; implants, including microimplants; eye drops; synthetic polymers; microspheres; nanoparticles; and the like.

The consumable matrix, in one embodiment, is designed to give a person more energy, keep the person alert, activate the body's natural chemicals that prevent depression and anxiety, and increases the consumer's libido and empathy. In an exemplary implementation, a composition provided may include the following components: Phenylethylamine (hereinafter referred to as "PEA"), Nicotinamide Mononucleotide (hereinafter referred to as "NMN") and/or Nicotinamide Riboside (hereinafter referred to as "NR"), Anthocyanin extract, Resveratrol, Pterostilbene, and Apigenin.

In the present invention, apigenin may be considered an integral component of the composition because of the benefits it provides in a two prong approach. As will be described in detail herein below, apigenin enhances the benefits of the other ingredients used in the composition, while simultaneously suppressing secondary side effects that may be caused as a result of their use. For reference, below is the structure of apigenin.

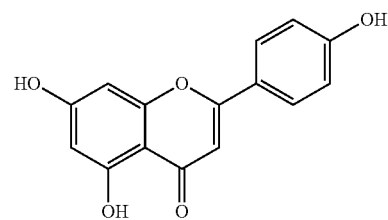 [SMILES: O=c1cc(-c2ccc(O)cc2)oc2cc(O)cc(O)c12]

With reference to FIG. 1, in the exemplary implementation, apigenin inhibits or kills the effects of enzyme CD38. Naturally, without CD38 inhibition, CD38 is responsible for breaking down nicotinamide adenine dinucleotide or NAD+. NAD+ is a cofactor that is central to energy metabolism and energy production. Inhibiting CD38 leads to an increase in NAD+, which subsequently leads to an increase of energy production. NAD+ is also known to stabilize telomeres, a compound structure that protects and diminishes the deterioration of cells (i.e., cellular aging).

NAD+ is also responsible for activating sirtuins. Sirtuins are a family of proteins that regulate health by regulating cell homeostasis. Of the family of seven sirtuins, studies have shown that sirtuins 1 and 6 show the greatest promise in improving human life and health. Accordingly, resveratrol, pterostilbene, and anthocyanin may be added to the composition to activate sirtuins 1 and 6. In particular, anthocyanin is used as an activator of sirtuin 6 and resveratrol is used as an activator of sirtuin 1. Generally, sirtuins, and in this particular case sirtuins 1 and 6, can only be activated in the presence of NAD+. Apigenin, as mentioned heretofore, increases the natural levels of NAD+ by inhibiting enzyme CD38 which breaks down NAD+. The natural increase in NAD+ allows for more activation of proteins. To further activate sirtuins 1 and 6, however, precursors such as NMN and/or NR may be added to the formulation. These precursors are the building blocks of NAD+, without them, additional NAD+ molecules would not form as abundantly.

The natural increase of NAD+ brings about may positive benefits outlined here and known in the art, however, its increase can have an effect on methylation. Methylation is the transfer of a methyl group, i.e., one carbon and three hydrogens, from one molecule to another in the body. Such transfer is a fundamental element to our biochemistry. Indeed, methylation is involved in the processes that create neurotransmitters, antioxidants, serotonin, melatonin, and other important and necessary substances in the body. Methylation also helps with detoxifying substances from the liver and tissue, including estrogen that can lead to cancer and neurotransmitters. NAD+ stresses the process of methylation by affecting the molecules that donate methyl groups, known as "methyl pools." Accordingly, in one exemplary embodiment, to counteract the decrease of methyl pools, Trimethylglycine and Betaine Anhydrous (TMG) may be added to the formulation. TMG provides methyl groups that can aid or supplement for lost molecules due to the increase in NAD+. In one exemplary form, the formulation may include between about 500 milligrams to about 2,500 milligrams of TMG.

With continued reference to FIG. 1, apigenin blocks the monoamine oxidase B enzyme (hereinafter referred to as "MAOB") that is naturally produced in the body. MAOB, if unchecked degrades the production levels of PEA and dopamine, and the absorbability of PEA. PEA is a chemical compound found naturally in the body that stimulates the production of chemicals that play a role in decreasing depression and other psychiatric conditions. Dopamine, an organic compound commonly referred to as the "pleasure" molecule motivates salience. In other words, dopamine regulates the intensity of behaviors that facilitate attainment of a particular goal. The increase levels of PEA and dopamine elicit an increased libido, especially for female consumers that suffer from a low libido. For men, testosterone shots or consumables are generally used to boost testosterone levels, which boosts the libido. For women, however, raising their libido through testosterone is not an option as high levels of testosterone in a woman may bring about unwanted effects, such as hair growth, deepening of the voice, acne, and other undesired side-effects. Accordingly, PEA is used in the present invention to boost the woman's libido without raising her testosterone levels. Increased levels of PEA and dopamine also improve the consumer's mood, which contributes to the euphoric feeling of "runner's high" that is generally considered an empathogen that produces an experience of emotional communion, openness, and relatedness. A form of synthesized PEA may also be added to the composition to further heighten the aforementioned effects that are felt when the body has an elevated level of PEA and dopamine. Unlike other MAOB inhibitors that combine with PEA that prove to be over-stimulatory at times, apigenin helps moderate excessive stimulation, and thus, prevents anxiety feelings that would otherwise ensue from a MAOB inhibitor. The present composition may also suppress the consumer's appetite and increase tactile sensations. As a result, the consumer may experience weight loss and generally have a positive mood.

In an alternative embodiment, the present composition may include PEA, NMN, and/or NR, anthocyanin extract, resveratrol, apigenin, gynostemma, fisetin, silymarin and sulforaphane. In particular, gynostemma, fisetin, silymarin and sulforaphane are plant-based compounds that activate or promote the body's production of 5' adenosine monophosphate-activated protein kinase (hereinafter referred to as "AMPK"). AMPK is an enzyme that plays a role in cellular energy homeostasis, and is important in the NAD+ sirtuin 1 cycle. AMPK regulates energy levels by breaking down energy stores and releasing ATP (or adenosine triphosphate—a complex organic chemical that provides energy to drive many processes in living cells), along with shutting down other pathways that consume ATP. As a result, more ATP is available for use, giving the consumer more energy.

Example embodiments are directed to compositions or formulations that include ingredients for the enhancement of energy, alertness, weight loss, appetite suppression, anti-anxiety and anti-depressant, and increased libido for male and females. Accordingly, in non-limiting example embodiments, compositions provided herein may include core ingredients, and optional ingredients.

As shown below, Table 1 illustrates a first exemplary implementation of the components of the consumable matrix or formulation:

TABLE 1

| Composition | |
|---|---|
| Ingredients | Amount (grams) |
| Apigenin | 1.0 g to 5.0 g |
| Phenylethylamine (PEA) | 0.05 g to 1.5 g |
| Nicotinamide Mononucleotide (NMN) | 0.15 g to 10.0 g |
| Anthocyanin extract (>25%) | 0.5 g to 2.0 g |
| Resveratrol | 0.5 g to 2.0 g |
| Pterostilbene | 0.05 g to 0.25 g |
| Piceatonnol | 0.02 g to 0.15 g |
| Total Weight | 2.72 g to 24.40 g |

In particular, the composition may include the amounts of apigenin within about 1.0 g to about 5.0 g, PEA within about 0.05 g to about 1.5 g, nicotinamide mononucleotide or NMN within about 0.15 g to about 5.0 g, and resveratrol within about 0.5 g to about 2.0 g. In an alternative exemplary form, Nicotinamide Riboside or NR within about 0.15 g to about 10.0 g may be used in addition to NMN. Alternatively, NR may be used instead of NMN. Further still, in another exemplary implementation of the present invention anthocyanin extract greater than 25% may be added to the composition within about 0.5 g to about 2.0 g. Additionally Pterostilbene within about 0.05 g to about 0.25 g and Piceatonnol within about 0.02 g to about may be used.

As shown below, Table 2 illustrates a second exemplary implementation of the components of the consumable matrix or formulation:

TABLE 2

| Composition | |
|---|---|
| Ingredients | Amount (grams) |
| Apigenin | 1.0 g to 10.0 g |
| Phenylethylamine (PEA) | 0.05 g to 1.5 g |
| Nicotinamide Mononucleotide (NMN) | 0.15 g to 5.0 g |
| Anthocyanin extract (>25%) | 0.5 g to 2.0 g |
| Resveratrol | 0.5 g to 2.0 g |
| Gynostemma | 0.15 to 1.0 g |
| Fisetin | 0.1 g to 0.5 g |
| Sulforaphane | 0.15 g to 0.5 g |
| Silymarin | 0.25 to 1.0 g |
| Carnosine | 0.5 g to 1.0 g |
| Total Weight | 3.8 g to 28 g |

In this particular exemplary composition, the composition may include the amounts of apigenin within about 1.0 g to about 10.0 g, PEA within about 0.05 g to about 1.5 g, NMN within about 0.15 g to about 5.0 g, anthocyanin extract greater than 25% within about 0.5 g to about 2.0 g, and resveratrol within about 0.5 g to about 2.0 g. Again, NR within about 0.15 g to about 5.0 g may be used in addition or instead of NMN. The composition may also include gynostemma within about 0.15 g to about 1.0 g, fisetin within about 0.1 g to about 0.5 g, sulforaphane within about 0.15 g to about 0.5 g, and silymarin within about 0.25 to about 1.0 g. As mentioned above, gynostemma, fisetin, sulforaphane, and silymarin may be added to the composition to promote the activation of AMPKs, which its increase lead to a myriad of benefits listed above. In an alternative exemplary composition, carosine within about 0.5 g to about 1.0 g may be added to the composition. Carosine is a molecule that may be used to increase the Hayflick limit of cellular senescence (i.e., increases the amount of times a cell can be divided). As an added benefit, carnosine clears the body of advanced glycation end products or AGEs for short. AGEs are known to contribute to oxidant stress and inflammation and are linked to diabetes and cardiovascular diseases.

As shown below, Table 3 illustrates a third exemplary implementation of the components of the consumable matrix or formulation:

TABLE 3

| Composition | |
| --- | --- |
| Ingredients | Amount (grams) |
| Apigenin | 1.0 g to 10.0 g |
| Phenylethylamine (PEA) | 0.05 g to 1.5 g |
| Nicotinamide Mononucleotide (NMN) | 0.15 g to 5.0 g |
| Anthocyanin extract (>25%) | 0.5 g to 2.0 g |
| Resveratrol | 0.5 g to 2.0 g |
| Liposomal GHK-Cu | 0.05 g to 0.25 g |
| GHK | 0.15 g to 0.5 g |
| Collagen Peptides | 5.0 g to 30.0 g |
| Liposomal Vitamin C | 0.5 g to 10.0 g |
| Total Weight | 8.35 g to 64.75 g |

In this particular exemplary composition, the composition may include the amounts of apigenin within about 1.0 g to about 10.0 g, PEA within about 0.05 g to about 1.5 g, NMN within about 0.15 g to about 5.0 g, anthocyanin extract greater than 25% within about 0.5 g to about 2.0 g, and resveratrol within about 0.5 g to about 2.0 g. Again, NR within a about 0.15 g to about 5.0 g may be used in addition or instead of NMN. The composition may also include liposomal GHK-Cu within about 0.05 g to about 0.25 g, non-copper GHK within about 0.15 g to about 0.5 g, collagen peptides within about 5.0 g to about 30.0 g, and liposomal vitamin C within about 0.5 g to about 10.0 g. In this particular implementation, the present composition enhances tissue recovery from an acute injury and promotes hair and nail growth. Moreover, the present composition may improve genetic behavior that leads to cellular and cognitive improvements, i.e., resetting genes to a more healthier and youthful state.

As shown below, Table 4 illustrates a fourth exemplary implementation of the components of the consumable matrix or formulation:

TABLE 4

| Composition | |
| --- | --- |
| Ingredients | Amount (grams) |
| Apigenin | 1.0 g to 10.0 g |
| Phenylethylamine (PEA) | 0.05 g to 1.5 g |
| Nicotinamide Mononucleotide (NMN) | 0.15 g to 5.0 g |
| Anthocyanin extract (>25%) | 0.5 g to 1.0 g |
| Resveratrol | 0.5 g to 1.5 g |
| Hydroxymethylbutyrate | 3.0 g to 5.0 g |
| Creatine | 3.0 g to 5.0 g |
| Leucine | 3.0 g to 5.0 g |
| Total Weight | 11.65 g to 37.5 g |

In this particular exemplary composition, the composition may include the amounts of apigenin within about 1.0 g to about 10.0 g, PEA within about 0.05 g to about 1.5 g, NMN within about 0.15 g to about 5.0 g, anthocyanin extract greater than 25% within about 0.5 g to about 1.0 g, and resveratrol within about 0.5 g to about 1.5 g. Again, NR within a range of about 0.15 g to about 5.0 g may be used in addition or instead of NMN. The composition may also include hydroxymethylbutyrate within about 3.0 g to about 5.0 g, creatine within about 3.0 g to about 5.0 g, and leucine within about 3.0 g to about 5.0 g. This implementation is designed for consumers that are into fitness because it promotes muscle synthesis. This composition, along with the exemplary compositions aforementioned, may be micro-encapsulated to prolong their timed release, which in-turn, prolongs their efficacy and block the unsavory taste of some of the ingredients.

Again, the unique consumable matrix of the present invention as described herein above lends itself to production in a variety of forms that can be mixed with a variety of consumables, such as beverages, jells, or mixable powders. Furthermore, when consumed the composition functions to increase the consumer's level of energy, alertness, and libido without the myriad of side effects caused by other formulations. It is also true that the present invention is designed to serve as an aid to overall greater health span through the anti-cancer, anti-diabetes, and anti-inflammatory nutraceutical consumable composition. The nutraceutical composition is also designed to suppresses the chemicals that are responsible for mood swings, anxiety, and depression giving the consumer a more positive mood—which improves their quality of life.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A nutraceutical formulation in a time release delivery that provides a person suffering from fatigue with alertness and energy, comprising:
    an enzyme inhibitor comprising apigenin; and
    a stimulant comprising phenylethylamine to co-stimulate energy level with the enzyme inhibitor,
        wherein a therapeutic effective amount of the enzyme inhibitor is selected from about 1 gram to about 10 grams combined with a therapeutic effective amount of the stimulant increase the person's energy level and alertness level.

2. The nutraceutical formulation of claim 1, wherein the enzyme inhibitor inhibits the effects of enzyme CD38 responsible for the breakdown of NAD+ and thus creating an increase of NAD+ within the person, the increase of NAD+ stabilizing the person's telomers that protect or lessen the deterioration of cells.

3. The nutraceutical formulation of claim 1, wherein the enzyme inhibitor moderates over stimulation by inhibiting the effects of monoamine oxidase B enzymes that when combined with the phenylethylamine cause undesired stimulation.

4. The nutraceutical formulation of claim 1, wherein the effective amount of apigenin is about 1 gram to about 5 grams.

5. The nutraceutical formulation of claim 1, wherein a unit dosage of the formulation contains a therapeutic effective amount of phenylethylamine.

6. The nutraceutical formulation of claim 5, wherein the therapeutic effective amount of phenylethylamine is about 50 milligrams to about 1.5 grams.

7. The nutraceutical formulation of claim 6, wherein the unit dosage of nutraceutical formulation is provided in encapsulated form.

8. The nutraceutical formulation of claim 1, further comprising a methylation supplement comprising trimethylglycine and betaine anhydrous.

9. The nutraceutical formulation of claim 8, wherein a unit dosage of the formulation contains a therapeutic effective amount of the trimethylglycine and betaine anhydrous to supplement depleted methyl pools because of an increase of NAD+ due to the stimulant and to aid in the detoxification of organs and tissue of the person.

10. The nutraceutical formulation of claim 9, wherein the therapeutic effective amount of the trimethylglycine and betaine anhydrous is about 500 milligrams to about 2,500 milligrams.

11. The nutraceutical formulation of claim 1, further comprising a protein promoter comprising one or more of anthocyanin extract, gynostemma, fisetin, silymarin, sulforaphane, and nicotinamide mononucleotide or nicotinamide riboside.

12. The nutraceutical formulation of claim 11, wherein the protein promotor promotes the production of 5' adenosine monophosphate-activated protein kinase (AMPK).

13. The nutraceutical formulation of claim 1, further comprising an antioxidant component comprising one or more of resveratrol, piceatannol, and pterostilbene.

14. A nutraceutical formulation that provides a person suffering from some degree of fatigue with alertness and energy, the formulation comprising:
an enzyme inhibitor comprising apigenin wherein a therapeutic effective amount of the enzyme inhibitor is selected from about 1 gram to about 10 grams;
an organic stimulant component comprising phenylenthylamine to co-stimulate energy level with the enzyme inhibitor;
a protein promotor comprising one or more of anthocyanin extract, gynostemma, fisetin, silymarin, sulforaphane, and nicotinamide monoucleotide or nicotinamide riboside; and
a methylation supplement comprising trimethylglycine and betaine anhydrous,
wherein the combination of the components decreases cellular degeneration, increases the person's energy level and alertness level and provides the person with the desire to engage in intimate sexual activity.

15. The nutraceutical formulation of claim 14, wherein a unit dosage of the formulation contains a therapeutic effective amount of the apigenin at about 1 gram to about 5 grams.

16. The nutraceutical formulation of claim 14, wherein a unit dosage of the formulation contains a therapeutic effective amount of the phenylethylamine at about 50 milligrams to about 1.5 grams.

17. The nutraceutical formulation of claim 14, wherein a unit dosage of the formulation contains a therapeutic effective amount of the trimethylglycine and betaine anhydrous at about 500 milligrams to about 2,500 milligrams to supplement depleted methyl pools because of an increase of NAD+ due to the organic stimulant.

18. The nutraceutical formulation of claim 14, wherein a unit dosage of the formulation contains a therapeutic effective amount of the one or more of anthocyanin extract, gynostemma, fisetin, silymarin, sulforaphane, and nicotinamide mononucleotide or nicotinamide riboside, the therapeutic effective amount is
about 0.5 grams to about 2 grams of the anthocyanin extract,
about 0.15 grams to about 1 gram of the gynostemma,
about 0.1 grams to about 0.5 grams of the fisetin,
about 0.25 grams to about 1 gram of the silymarin,
about 0.15 grams to about 0.5 grams of the sulforaphane, and
about 0.15 grams to about 5 grams of the nicotinamide mononucleotide, or about 0.15 grams to about 5.0 grams of the nicotinamide riboside.

19. A nutraceutical formulation that provides a person suffering from some degree of fatigue with alertness and energy, the formulation comprising:
an enzyme inhibitor comprising apigenin;
a synthetic or organic stimulant comprising phenylethylamine to co-stimulate energy level with the enzyme inhibitor;
a protein promoter comprising one or more of anthocyanin extract, gynostemma, fisetin, silymarin, sulforaphane, and nicotinamide mononucleotide or nicotinamide riboside;
a methylation supplement comprising trimethylglycine and betaine anhydrous; and
an antioxidant component comprising one or more of resveratrol, piceatannol, and pterostilbene,
wherein the combination of the components decreases cellular degeneration, increases the persons' feelings of euphoria, empathy, energy level, alertness level and libido, and provides the person with the desire to engage in intimate sexual activity and other physical activity, and
wherein the formulation is in a unit dosage selected from a therapeutic effective amount of,
about 1 gram to about 5 grams of the apigenin,
about 50 milligrams to about 1.5 grams of the phenylethylamine,
about 0.5 grams to about 2 grams of the anthocyanin extract,
about 0.15 grams to about 1 gram of the gynostemma,
about 0.1 grams to about 0.5 grams of the fisetin,
about 0.25 grams to about 1 gram of the silymarin,
about 0.15 grams to about 0.5 grams of the sulforaphane, and
about 0.15 grams to about 10 grams of the nicotinamide mononucleotide or about 0.5 grams to about 1.5 grams of the nicotinamide riboside,
about 500 milligrams to about 2.5 grams of the trimethylglycine and betaine anhydrous,
about 0.5 grams to about 2 grams of the resveratrol,
about 0.02 grams to about 0.15 grams of the piceatannol, and
about 0.05 grams to about 0.25 grams of the pterostilbene.

* * * * *